United States Patent [19]

Schade et al.

[11] Patent Number: 4,535,248

[45] Date of Patent: Aug. 13, 1985

[54] METHOD FOR DETECTING AFLATOXIN IN ALMONDS

[75] Inventors: John E. Schade, Walnut Creek; A. Douglas King, Jr., Martinez, both of Calif.

[73] Assignee: The United States of America as represented by the Secretary of Agriculture, Washington, D.C.

[21] Appl. No.: 643,990

[22] Filed: Aug. 24, 1984

[51] Int. Cl.$^3$ ...................... G01N 21/33; B07C 5/342
[52] U.S. Cl. ............................... 250/459.1; 250/461.2
[58] Field of Search ............... 250/459.1, 461.2, 458.1, 250/461.1

[56] References Cited

U.S. PATENT DOCUMENTS 4,000,975  1/1977  Christenbury et al. ............. 250/265
4,203,522  5/1980  Fraenkel et al. .................... 250/226
4,436,756  3/1984  Canella et al. ...................... 426/430

FOREIGN PATENT DOCUMENTS 993063  5/1965  United Kingdom ............. 250/461.2

OTHER PUBLICATIONS

J. E. Schade, K. McGreevy, A. D. King, Jr., B. Mackey, and G. Fuller, "Incidence of Aflatoxin in California Almonds", *Applied Microbiology*, 29 (1): 48–53, (1975).
G. Fuller, W. W. Spooncer, A. D. King, Jr., J. Schade, and B. Mackey, "Survey of Aflatoxins in California Tree Nuts", *Journal of the American Oil Chemists' Society*, 54 (3): 231A–234A, (1977).
A. F. Cucullu, L. S. Lee, R. Y. Mayne, and L. A. Goldblatt, "Determination of Aflatoxin in Individual Peanuts and Peanut Sections", *Journal of the American Oil Chemists' Society*, 43 (2): 89–92, (1966).
E. H. Marth, "Aflatoxins and Other Mycotoxins in Agricultural Product", *Journal of Milk and Food Technology*, 30: 192–198, (1967).
J. J. Wong and D. P. H. Hsieh, "Mutagenicity of Aflatoxins Related to Their Metabolism and Carcinogenic Potential", *Proceedings of the National Academy of Science, USA*, 73 (7): 2241–2244, (1976).
L. J. Ashworth, Jr. and J. L. McMeans, "Association of *Aspergillus flavus* and Aflatoxins with a Greenish Yellow Fluorescence of Cotton Seed", *Phytopathology*, 56: 1104–1105, (1966).
O. L. Shotwell, M. L. Goulden, and C. W. Hesseltine, "Aflatoxin Contamination: Association with Foreign Material and Characteristic Fluorescence in Damaged Corn Kernels", *Cereal Chemistry*, 49: 458–465, (1972).
J. W. Dickens and R. E. Welty, "Fluorescence in Pistachio Nuts Contaminated with Aflatoxin", *Journal of the American Oil Chemists' Society*, 52: 448–450, (1955).
A. Kornerup and J. H. Wanscher, *Methuen Handbook of Color*, 3rd Edition, Eyre Methuen, London (1978).
"Mycotoxins Methodology", 13th Edition, *Association of Official Analytical Chemists*, AOAC, Chapter 26, pp. 1–7, (1980).
R. M. Beebe, "Reverse Phase High Pressure Liquid Chromatographic Determination of Aflatoxins in Foods", *Journal of the Association of Official Analytical Chemists*, 61 (6): 1347–1352, (1978).
D. M. Takahashi, "Reversed-Phase High-Performance Liquid Chromatographic Analytic System for Aflatoxins in Wines with Fluorescence Detection", *Journal of Chromatography*, 131: 147–159, (1977).

*Primary Examiner*—Alfred E. Smith
*Assistant Examiner*—Carolyn E. Fields
*Attorney, Agent, or Firm*—M. Howard Silverstein; David G. McConnell; Margaret A. Connor

[57] ABSTRACT

Aflatoxin contamination in almonds is detected by exposing almond kernels to long wave ultraviolet light and detecting the presence of aflatoxin as determined by violet-purple fluorescence. The method is particularly adaptable to automation to detect and sort out aflatoxin contaminated almonds.

10 Claims, No Drawings

4,535,248

METHOD FOR DETECTING AFLATOXIN IN ALMONDS

BACKGROUND OF THE INVENTION

This invention relates to and has among its objects the provision of a novel method for detecting aflatoxin contamination in almonds.

Aflatoxins, a group of highly toxic substances produced by certain species of Aspergillus, especially *A. flavus*, have been found to occur in agricultural products such as corn, cottonseed, a variety of oilseeds, and many varieties of nuts. Experimental studies indicate that aflatoxins are acutely toxic to most animal species. The extreme toxicity of aflatoxin is demonstrated by the fact that the $LD_{50}$ of the $B_1$ component is less than 30 micrograms for day-old ducklings. Animals which consume sublethal quantities of aflatoxin for several days or weeks develop a subacute toxicity syndrome which commonly includes moderate to severe liver damage. Prolonged administration of the toxin at subacute levels leads to formation of cancerous liver tumors. Data accumulated from feeding tests indicate that the effective dose of the $B_1$ component of aflatoxin for the induction of liver tumors in rats is approximately 10 mg per day. When this value is compared with similar estimates for other hepatocarcinogens such as dimethylnitrosamine (750 mg/day) and butteryellow (9,000 mg/day), the relative potency of aflatoxin is readily apparent.

Aflatoxins occur at varying concentrations throughout the tissue of contaminated products and can occur at concentrations up to over 1,000,000 parts per billion (ppb) in individual nuts such as peanut kernels. These toxins may remain after the molds that produced them are removed or destroyed. Aflatoxins are fairly resistant to heat and to chemical treatments that do not destroy the nutmeat. conventional food processing, such as roasting nuts, can reduce the aflatoxin level but not sufficiently to solve the problem.

Aflatoxin contamination has been found in tree nuts such as walnuts and almonds. Infection of tree nuts with aflatoxigenic molds probably occurs most often in the field before and/or during harvest while the kernels are still moist. Intact shells appear to protect nuts from mold but damage to the shell by mechanical harvesting or insect infestation allow the mold to proliferate on the kernels while the nuts are still moist. In particulate foods, such as nuts, the toxins are confined to a relatively few units, and the solution to the aflatoxin problem is the removal of the contaminated units. In a survey of the almond crop in California, it was estimated that before processing about one kernel in 26,500 in-shell almonds is contaminated with aflatoxin; however, these kernels have, on the average, very high levels of aflatoxin, and thus it is essential that all contaminated nuts are removed.

Presently shelled almonds are sorted by a combination of electronic color sorting and manual sorting by trained personnel. Because aflatoxin content in almonds appears to be correlated with the number of seriously damaged kernels, removal of these kernels by commercial sorting procedures appreciably reduces aflatoxin contamination. However, because of the acute toxicity, mutagenicity, and carcinogenicity of aflatoxin, it is important that the removal of this toxin be maximized. Additionally, it is a common practice to use less seriously damaged kernels, i.e., almonds which are chipped or broken or have other minor damage affecting their appearance, to manufacture sliced and diced nuts, and this practice tends to increase the chance of aflatoxin contamination of such products due to the unavoidable inclusion of some seriously damaged nuts with the less damaged nuts normally used as manufacturing stock; even the standards for the best quality grades of shelled almonds include some tolerance for the inadvertent inclusion of seriously damaged kernels. Although there has been a long felt need, heretofore no ready method for detection of aflatoxin contamination in almonds has been known.

Studies on cottonseed and corn have shown that seed contaminated with *A. flavus* are often associated with a bright greenish-yellow (BGY) fluorescence. Investigators have reported that *A. flavus* isolated from BGY fluorescent cotton fibers produced kojic acid, which was converted to the BGY fluorescing substance by plant tissue peroxidase. In a study of pistachio nuts, kernels from nuts showing BGY fluorescence contained 50% of the aflatoxin in the samples studied. However, because *A. flavus* grew from only 21% of the kernels from fluorescent shells and 4% of the BGY fluorescent shells, the researchers concluded that fungi other than *A. flavus* produced BGY fluorescence in pistachio shells, but that BGY fluorescence may indicate that conditions have been favorable for growth of toxicogenic molds on pistachio nuts. Though the preceding was known, this information did not disclose or suggest any method for detecting aflatoxin contamination in almonds.

SUMMARY OF THE INVENTION

We have now discovered a method for detecting aflatoxin contamination in almonds. Our method comprises exposing almond kernels to long wave ultraviolet light and detecting aflatoxin contamination as determined by violet-purple fluorescence.

The ability to detect aflatoxin on almond kernels by violet-purple fluorescence was totally unexpected. Of the four naturally occurring components of aflatoxin, crystalline $B_1$ and $B_2$ exhibit a blue fluorescence under long wave ultraviolet light, and $G_1$ and $G_2$ exhibit a greenish-gold fluorescence. The mold *Aspergillus flavus*, which produces aflatoxin, does not fluoresce. As stated previously, BGY fluorescence has been reported to show some relationship to aflatoxin contamination on some agricultural commodities. One theory is that the BGY fluorescence is related to kojic acid which is produced by *A. flavus* or a metabolite of kojic acid formed upon contact with the agricultural commodity. No violet-purple fluorescence was heretofore reported for aflatoxin contamination. It is not known what compound or compounds causes the violet-purple fluorescence on almond kernels contaminated with aflatoxin. Surprisingly however, all kernels having aflatoxin contamination fluoresced violet-purple under long wave UV light and kernels showing bright yellow fluorescence showed no aflatoxin contamination.

The instant method is particularly adaptable to automation in combination with or in place of current commercial electronic almond-sorting machines.

In accordance with this discovery, it is an object of the invention to provide a method for the simple and rapid detection of aflatoxin in almonds.

It is another object of the invention to provide a fluorescent detection method for aflatoxin contamination in almonds which is suitable for automation and which can be readily adapted for use with existing electronic sorting machines.

Other objects and advantages of this invention will become readily apparent from the ensuing description.

DETAILED DESCRIPTION OF THE INVENTION

The instant invention for the first time provides a simple and rapid method to detect aflatoxin contamination in almonds. In the method of the invention, almond kernels are exposed to long wave ultraviolet light, and aflatoxin contamination on the kernels is detected by violet-purple fluorescence.

Almond kernels where the pellicle is broken or absent show intense fluorescence which may be white, blue or yellow. We have found that if violet-purple fluorescence is seen, then the kernel has aflatoxin contamination. Whole almonds having healthy intact pellicles show no fluorescence.

In our method, almond kernels are exposed to long wave ultraviolet light, commonly called "black light". The wavelength is about 365 nm but may range between 320 and 400 nm. The violet-purple fluorescence which relates to aflatoxin contamination is determined visually. A precise determination of the fluorescence may be made by use of the *Methuen Handbook of Color,* 3rd Edition, by Kornerup and Wanscher, Eyre Methuen, London (1978). In the Methuen color code notation, hue is represented by a number (1–30), tone by a letter (A–F) with the amount of black increasing from A to F, and intensity by another number (1–8) with color saturation increasing from 1 to 8. We found that samples having a violet-purple color defined by the Methuen code as having a hue of 13 to 18, a tone of A to C, and an intensity of 4–7 showed aflatoxin contamination. Color determination to detect violet-purple fluorescence equivalent to that of the Methuen code numbers named above may be made by other techniques known to those skilled in the art such as observing the emission spectra using a spectrophotofluorometer.

This invention is particularly adaptable to automation. For example, electronic sorting machines can be equipped with a black light to sort out almonds showing violet-purple fluorescence. A particularly useful way to use the invention would be to combine it with current electronic sorting machines. In this use, the current electronic sorting machine would sort out all damaged kernels, and the damaged kernels would be sorted for aflatoxin contamination by the method of the invention. In this manner, incidental inclusion of aflatoxin contamination in sliced or diced almond products would be greatly reduced.

The method of the invention is next demonstrated by the following illustrative example.

EXAMPLE a. Almond selection. Individual kernels or kernel pieces which showed violet-purple, yellow or vivid blue fluorescence under long wave (365 nm) UV light, using a Chromato-Vue Chamber, Model C-6 (Ultra Violet Products, Inc., San Gabriel, CA) were chosen for aflatoxin analysis.

b. Almond samples. Individual kernels or kernel fragments with distinct fluorescent colors were selected for analysis from samples of blanched whole almonds, rejected blanched whole almonds, or rejected shelled almonds. The latter almonds had "serious damage," which includes decay, insect injury, and mold damage (U.S. Standards for Grades of Shelled Almonds, 25F.R. 7273, Aug. 15, 1960). In general, individual kernels were badly scratched, chipped, or broken. Sometimes a kernel was divided into fluorescent colored and colorless portions for analysis, or the colored portions of several similar kernels were combined for analysis.

c. Description of fluorescent colors. Colors were determined visually. Initially, descriptions of fluorescent color were in general lay terms. Later, color was described more precisely by means of color charts in the *Methuen Handbook of Color.* Color was recorded using Methuen notation wherein hue is represented by a number (1–30), tone by a letter (A–F), and intensity by another number (1–8).

d. Aflatoxin analysis. Each kernel or group of kernel pieces was placed on a hardened filter paper (S&S No. 576, 9 cm) in a petri dish and cut with a razor blade until a fine meal was obtained. A weighed amount of the sample (1 g or less) was mixed with 0.5 g Hyflo Super Cel (celite) plus 0.5 ml distilled water plus 6–10 ml chloroform in a 125 ml glass-stoppered Erlenmeyer flask, which was placed on a wrist action shaker for 55 min. The sample was filtered through E&D fluted filter paper #515 (cut to about 8 cm diameter to conserve filtrate) into a 10 ml graduated cylinder. With its volume noted, the filtrate, or a measured volume of it, was added to the top of a Sep Pak silica cartridge (Waters Assoc., Milford, MA). The silica cartridge was washed with 1 ml chloroform followed by 2 ml hexane and 4 ml ether. Aflatoxins were eluted from the cartridge with 4 ml chloroform-methanol (85:15) into a small vial. The sample was evaporated to dryness with a stream of nitrogen and then dissolved in 0.2–2 ml of 98:2 benzene-acetonitrile for thin layer chromatography (TLC) analylsis. After each aflatoxin was estimated by TLC, the sample was evaporated to dryness under nitrogen. To avoid occlusion of aflatoxins by waxy materials present, 300 $\mu$l hexane was added prior to adding 100 or 200 $\mu$l trifluoroacetic acid (TFA) to derivatize any aflatoxins $B_1$ and $G_1$ present to $B_{2a}$ and $G_{2a}$. An appropriate dilution for high performance liquid chromatography (HPLC) analysis was made with 0.5–10 ml water-acetonitrile (90:10). Usually, a final filtration was made with a Millex-SR 0.5 $\mu$m filter unit or similar polytetrafluoroethylene membrane filter (prewetted with methanol).

f. High performance liquid chromatography. HPLC, which was used for quantitative analysis, was conducted with a reversed phase column procedure similar to that of Beebe, *Journal of the Association of Official Analytical Chemists,* 61(6):1347–1352 (1978) using two HPLC systems. In both systems aflatoxin concentration was determined from its peak area relative to that of an external aflatoxin standard run consecutively.

The first system consisted of a 5 $\mu$m Spherisorb ODS column, 4.6 mm i.d.×25 cm (Applied Science Labs., Inc. State College, PA) connected to a Waters Model U6K injector equipped with a 2 ml loop and a Waters Model 6000A solvent pump (Waters Associates, Milford, MA). Detection was by means of a Schoeffel FS970LC Fluoromonitor and a GM970 monochromator (Schoeffel Instruments, Div. of Kratos, Inc. Westwood, NJ) with excitation set at 360 nm and a 418 nm emission cutoff filter. Quantification was accomplished with an Esterline Angus Model L1102S recorder/integrator (Esterline Corp. Indianapolis, IN). Injection volume was 5–20 $\mu$l. Development was with wateracetonitrile-methanol (71:19:10) at a flow rate of 1.5 ml/min.

The second system consisted of a 10 μm Bondapak $C_{18}$ column, 3.9 mm i.d.×30 cm (Waters Assoc., Milford, MA) connected to a Rheodyne Model 7125 injection valve (Rheodyne, Inc., Cotati, CA) equipped with a 20 μl injection loop and a Beckman Model 110A metering pump (Beckman Instruments, Fullerton, CA). Development was with water-acetonitrile-methanol (70:15:15) at a flow rate of 1.5 ml/min. Detection was by means of an Aminco Fluoromonitor (American Instruments Co., Silver Spring, MD) equipped with a Corning #7-60 primary filter (360 nm excitation) and a Wratten No. 2A (418 nm cutoff) secondary filter. An ISCO Model 1840 variable wavelength absorbance monitor (Instruments Specialties Co., Lincoln, NE) was used concurrently to measure UV absorbance at 360 nm. Individual HP3390A integrators (Hewlett-Packard, Avondale, PA) were used to determine retention times and areas of peaks obtained With the two detectors. The fluorescence system was used for quantification, because it was more sensitive than the UV system. For a few samples with high levels aflatoxin, the retention time and area of peaks obtained with the UV system served as an additional check on peak identity. The second detector gave retention times of 7-8 seconds longer than the first.

g. Aflatoxin standards. The concentrations of solutions of the four individual aflatoxins (Applied Science Laboratories, Inc. State College, PA) were determined from their UV absorption according to the AOAC methods ("Mycotoxins Methodology," *Association of Official Analytical Chemist*, 13th Edition, Chapter 26, pp 1-7 AOAC, (1980)). A reference standard containing 1 μg of each aflatoxin per ml was prepared as follows for use in the first HPLC system: volumes of the standards equivalent to 10 μg of each aflatoxin were mixed together, evaporated to dryness under nitrogen, and treated with 300 μl TFA to convert the $B_1$ and $G_1$ to $B_{2a}$ and $G_{2a}$; the derivatized mixture was diluted with wateracetonitrile (90:10) to 10 ml and filtered through a 0.5 μm membrane filter.

Another derivatized standard was prepared in a similar manner for use in the second HPLC system from a commercial aflatoxin mixture (Applied Science Laboratories). This derivatized mixture was diluted to two different concentrations: (1) 100 ng each of $B_1$ and $G_1$ (as $B_{2a}$ and $G_{2a}$) plus 30 ng each of $B_2$ and $G_2$ per ml; (2) 10 ng each of $B_1$ and $G_1$ (as $B_{2a}$ and $G_{2a}$) plus 3 ng each of $B_2$ and $G_2$ per ml.

For reference, 10 μl of the first standard was injected in the first HPLC system, and 20 μl of one of the two dilutions of the second standard was used in the second system.

h. Mold identification. Mold cultures were isolated from individual moldy kernels by direct isolation technique, using malt agar, and were identified by growth on Czapek's agar.

i. NMR analysis. Nuclear magnetic resonance (NMR) spectra were run on a Varian EM-390 (Varian, Palo Alto, CA) equipped with a Nicolet 1180 computer (Nicolet Magnetics Corp., Fremont, CA) for rapid scan operation.

j. Blanched almonds. Commercially blanched (steamed to remove the pellicle) whole almonds (select grade) and blanched almonds rejected by a commercial processor during the sorting process were examined under UV light as described above. The results are given in Table 1. Many of the rejected kernels appeared bright blue or bright yellow, while some possessed both colors; none were greenish-yellow. The blue pieces varied in color intensity; the brightest ones remained blue under short-wave UV light. Two kernel fragments from the rejected almonds had a definite violet-purple color under long-wave UV light; these were cut and analyzed as one sample (11). One kernel of the select blanched kernels had a similar violet-purple color in a portion of it. This kernel (57) and another (58) from the select kernels that had a particularly bright blue area were divided into colored and colorless portions for separate analysis. Only the violet-purple kernels or kernels fragments had aflatoxin levels over 1000 ppb (Table 1). The violet-purple blanched kernels contained both aflatoxin $B_1$ and aflatoxin $B_2$ but no detectable amounts of the G-aflatoxins.

k. Damaged almonds. Aflatoxin contamination and fluorescent color of almond kernels having "serious damage" as described in b above are given in Table 2. All almonds having a violet-purple fluorescence had over 100,000 ppb total aflatoxins.

Two almond kernels (49 and 102) had visible mold growth, which proved to be *Aspergillus flavus* when cultured. The damaged edge of the first kernel (49) and most of the other kernel (102) appeared purple-violet under UV light. When split open, the center of the first kernel had a similar fluorescent purple-lilac color. On the basis of these observations, and the results of the previous analyses, it seemed likely that any almond with a violet-purple fluorescence on its exposed flesh would contain aflatoxin.

From the results in Tables 1 and 2, it appears that all kernels with a purplish-red to violet fluorescent color had over 100,000 ppb total aflatoxins. When a significant portion of a colored kernel lacked a distinct fluorescence, that portion had less aflatoxin than the colored portion (103a, b; 104a, b; 210a, b). None of these kernels contained aflatoxin $G_1$, and only one (210a) contained a compound identified by its retention times as aflatoxin $G_2$ (460 ppb). The purple-violet color group of kernels (Table 2) can be defined as having a hue of 13-18, a tone of A to C, and an intensity of 4-7.

TABLE 1

| Sample no. | Fluorescent color | Weight (g) | Source | Aflatoxin (ppb) $B_1$ | $B_2$ |
|---|---|---|---|---|---|
| 11 | Violet-Purple (2 pieces) | 0.77 | Reject | $9.71 \times 10^4$ | $1.48 \times 10^4$ |
| 12a | Bright Yellow portions | 1.00 | Reject | 70 | ND[a] |
| 12b | Bright Blue portions | 1.00 | Reject | ND | ND |
| 13 | Bright Blue portions | 1.00 | Reject | ND | ND |
| 57a | Violet-Purple portions | 0.24 | Select | $1.61 \times 10^5$ | $2.54 \times 10^4$ |
| 57b | Colorless portion | 0.19 | Select | ND | ND |
| 58a | Blue portion | 0.24 | Select | 50 | ND |
| 58b | Colorless portion | 0.64 | Select | 108 | ND |

[a] ND = Not detected, which indicates less than 20–40 ppb aflatoxin, depending on the sample weight and individual analysis. Aflatoxins $G_1$ and $G_2$ were not detected in any of these samples.

TABLE 2

| Sample no. | Fluorescent color Descriptive name | Methuen Code(s) | Weight (g) | Aflatoxin[1] (ppb) $B_1$ | $B_2$ |
|---|---|---|---|---|---|
| 49[2] | purple, lilac, greyish magenta to violet, and greyish violet | 15B6,16B4, (13–15)C(6–7) and (16–18)C5 | 0.73 | $1.05 \times 10^6$ | $9.10 \times 10^4$ |
| 101 | greyish violet | 14C6,15C5 | 0.67 | $1.77 \times 10^6$ | $1.33 \times 10^5$ |
| 102[2] | greyish magenta, reddish lilac, greyish violet, and purple | (13–15)C5 and 15C7 | 0.54 | $2.34 \times 10^6$ | $1.32 \times 10^5$ |
| 103a | violet-red to greyish magenta; darkens to violet | 14BC6 to 15C6 | 0.50 | $2.02 \times 10^5$ | $1.45 \times 10^4$ |
| 103b | colorless portion | — | 0.43 | $1.30 \times 10^2$ | ND[a] |
| 104a | violet-red with blue edge | 13B6 fresh cut surface | 0.37 | $4.97 \times 10^5$ | $4.99 \times 10^4$ |
| 104b | colorless portion | — | 0.19 | $2.17 \times 10^3$ | ND |
| 121a | blue | 21A8 | 0.98 | 125 | 100 |
| 121b | colorless; some brown in tungsten light | — | 0.67 | ND | ND |
| 122a | yellow; some brown in tungsten light | 3A6 | 0.44 | ND | ND |
| 122b | colorless | — | 0.33 | ND | ND |
| 123 | blue | 21A6,20B6 | 0.71 | ND | ND |
| 201 | reddish orange spots | 7A8 | 0.95 | ND | ND |
| 202 | reddish orange | 7A8 | 0.28 | ND | ND |
| 203 | blue | (20–21)A8 | 0.64 | ND | ND |
| 204 | blue | 21A8 | 0.47 | ND | ND |
| 205 | blue | 21B7 | 0.47 | ND | ND |
| 206 | blue | 21B7 | 0.84 | $9.0 \times 10^2$ | $2.3 \times 10^2$ |
| 207 | vivid yellow | 3A8 | 0.91 | 9 | ND |
| 208 | yellow, orange, and blue in same kernel | — | 0.56 | 11 | ND |
| 209 | pale yellow, pastel yellow; yellow & pink on fresh cut | 2A3 1A4 2A4 & 15B4 | 0.70 | 25 | ND |
| 210a | purple portion | 15B6 | 0.29 | $1.54 \times 10^5$ | $1.38 \times 10^4$ |
| 210b | colorless or pale yellow portion | — | 0.21 | $3.20 \times 10^4$ | ND |
| 212 | light lilac | (15–16)A(4–5) | 0.29 | $2.09 \times 10^5$ | $2.55 \times 10^4$ |
| 213 | pastel violet, light violet | (15–17)A4 | 0.80 | $3.77 \times 10^5$ | $6.00 \times 10^4$ |
| 214 | yellow | 3A(8–7) | 0.44 | 56 | 10 |
| 215 | vivid blue | (20–21)A8 | 0.38 | ND | ND |
| 216 | light violet & purplish pink | 18A5 & 14A3 | 1.03 | 3 | ND |
| 217 | pastel blue | (20–21)AB(4–5) | 0.58 | ND | ND |
| 218 | pastel blue | (20–21)AB(4–5) | 0.43 | ND | ND |
| 219 | pastel blue | (20–21)AB(4–5) | 0.40 | ND | ND |
| 220 | pastel blue | (20–21)AB(4–5) | 0.60 | ND | ND |
| 221 | orange spot | 7A7 | 0.40 | 3 | ND |
| 222 | orange spots (from 4 kernels) | 7A7 | 0.41 | 3 | ND |
| 223 | colorless portions from #222 | 6A3 & 22A3 | 1.50 | 3 | ND |
| 224 | yellow | 3A(7–8) | 0.34 | 8 | ND |
| 225 | orange spot | 7A6 | 0.51 | 4 | ND |
| 226 | orange spot (single large kernel) | 7B7 | 1.74 | ND | ND |

[a]ND = None detected i.e., less than 2–125 ppb present, depending on the samples; for samples 49–123, less than 100–125 ppb; for samples 201–226, less than 2–8 ppb.

Notes:
[1]Aflatoxin $G_1$ was not detected in any of these samples; aflatoxin $G_2$ was detected in only one sample (210a) at 460 ppb.
[2]Samples 49 and 102 represent 49 and 55%, respectively, of the weight of these kernels as found.

Any kernel having a fluorescent color in this "color area" should be suspected of containing aflatoxin. Two of the kernels (209 and 216) had a tinge of such color but had very low levels of aflatoxin; sample 209 showed only a tinge of this color on a fresh cut and was considered to belong to the yellow group, while sample 216 differed from the other kernels in the group in both tone and intensity. Kernels that had a blue hue free, or almost free, of red (e.g., Methuen hue 20–23) appeared to have relatively little or no aflatoxin. In summary, many almond kernels have a blue fluorescence, while very few had a purple-violet fluorescence.

Color groups of whole kernels other than blue, contained, with one exception, only aflatoxins $B_1$ and $B_2$. In most of these samples, aflatoxins $B_1$ and $B_2$ were identified by both TLC and HPLC. With a few samples the determination of aflatoxin concentration from UV peak, in addition to the fluorescence peak, served to confirm the identity of the $B_{2a}$ ($B_1$) and $B_2$ peaks. With two samples (101 and 102), the presence of aflatoxins $B_1$ and $B_2$ in their extracts was confirmed by observing proton NMR peaks characteristic of these compounds.

A summary of results of kernels is shown in Table 3. Four distinct fluorescent color groups are listed together with Methuen color notation to define the color areas represented by each group. A fifth color group contains one kernel (216) that was very similar to the violet-purple group on the basis of its hue but could be distinguished because of its difference in tone and intensity. The data in Table 3 have been recalculated from the assays, so that the aflatoxin concentration represents that in the kernel or kernel fragment as found, rather than that in the colored portion. If two kernel fragments were combined for analysis, the result was assumed to represent each fragment. By this approach, we estimated the range of aflatoxin concentration in contaminated kernel, which allowed us to compare these results with statistical estimates made in previous studies.

Although the number of kernels representing the various color groups is small (Table 3), it is obvious from the results that the violet-purple fluorescent kernels were invariably contaminated with aflatoxin and, therefore, should be sorted out. The total aflatoxin concentration found in these contaminated kernels ranged from $1.0 \times 10^5$ to $2.5 \times 10^6$ ppb; the mean and median concentrations were $4.8 \times 10^5$ and $1.8 \times 10^5$ ppb, respectively. These values are in general agreement with previous statistical estimates of the average aflatoxin concentration per contaminated kernel, calculated from average concentration per lot and estimated proportion of contaminated kernels. The statistical estimates, based on data with similar almonds from three crop years, ranged from $2.57 \times 10^5$ to $7.76 \times 10^5$ ppb and had a mean and median of $3.97 \times 10^5$ and $4.15 \times 10^5$ ppb, respectively.

The results of Table 1–3 indicate that almond kernels with violet-purple fluorescence contain aflatoxin, normally at over 100,000 ppb, and should be removed from edible nuts. The violet-purple nuts in this study generally did not have measurable levels of the G-aflatoxins. Some of the many almonds that fluoresce blue contain aflatoxins, but generally at levels below 200 ppb.

It is understood that the foregoing detailed description is given merely by way of illustration and that modification and variations may be made within, without departing from the spirit and scope of the invention.

TABLE 3

| Color group descriptive name | Number of kernels[a] | Number of assays | Methuen color | Aflatoxin range (ppb) | Average (ppb) | No. of kernels over 200 ppb |
|---|---|---|---|---|---|---|
| Yellow | 6 | 8 | (1–2)A(3–4) 3A(6–8) | 0–66 | 24 | 0 |
| Reddish-Orange fluorescent spots | 9 | 7 | 7A(6–8) 7B7 | 0–7 | 1 | 0 |
| Blue | 14 | 16 | (20–21)AB(4–5) | 0–1130 | 97 | 1 |
| Violet-Purple | 10 | 16 | (13–15)C(5–7) (13–15)B6 (15–16)AB(4–5) (16–18)C5 | $1.0 \times 10^5$ to $2.5 \times 10^6$ | $4.8 \times 10^5$ | 10 |
| Light violet with purplish pink | 1 | 1 | 18A5,14A3 | 3 | 3 | 0 |

[a]Kernels or fragments as found, before sectioning or combining for assay.

Having thus described our invention, we claim:

1. A method for detecting aflatoxin contamination in almonds, which comprises:
   (a) exposing almond kernels to long wave ultraviolet light and
   (b) detecting the presence of aflatoxin as determined by violet-purple fluorescence.

2. The method as described by claim 1 wherein the almond kernels comprise individual kernels or kernel fragments.

3. The method as described by claim 2 wherein the almond kernels comprise blanched almonds.

4. The method as described by claim 1 wherein the almond kernels comprise damaged kernels.

5. The method as described by claim 4 wherein damaged kernels comprise kernels having insect injury, decay, or mold damage.

6. The method as described by claim 1 wherein the violet-purple fluorescence is a purplish-red to violet fluorescent color defined by the Methuen color code as having a hue of 13–18, a tone of A to C, and an intensity of 4–7.

7. The method as described by claim 1 wherein the violet-purple fluorescence is equivalent to that defined by claim 6.

8. The method as described in claim 1 which is automated.

9. A method of reducing aflatoxin content in almonds, which comprises detecting aflatoxin contamination in almonds according to the method of claim 1 and sorting out the aflatoxin contaminated almonds.

10. The method as described in claim 9 which is automated.

* * * * *